(12) United States Patent
Sharzer et al.

(10) Patent No.: US 12,417,337 B2
(45) Date of Patent: *Sep. 16, 2025

(54) DATA NORMALIZATION AND IRREGULARITY DETECTION SYSTEM

(71) Applicant: Palantir Technologies Inc., Denver, CO (US)

(72) Inventors: Charles Sharzer, New York, NY (US); Meghana Bhat, New York, NY (US); William Brady, Washington, DC (US)

(73) Assignee: Palantir Technologies Inc., Denver, CO (US)

( * ) Notice: Subject to any disclaimer, the term of this patent is extended or adjusted under 35 U.S.C. 154(b) by 863 days.

This patent is subject to a terminal disclaimer.

(21) Appl. No.: 17/652,646

(22) Filed: Feb. 25, 2022

(65) Prior Publication Data

US 2022/0292250 A1    Sep. 15, 2022

Related U.S. Application Data

(63) Continuation of application No. 15/873,753, filed on Jan. 17, 2018, now Pat. No. 11,263,382.

(Continued)

(51) Int. Cl.
*G06Q 40/08*    (2012.01)
*G06F 3/0482*   (2013.01)
(Continued)

(52) U.S. Cl.
CPC ......... *G06F 40/103* (2020.01); *G06F 3/0482* (2013.01); *G06F 16/90332* (2019.01);
(Continued)

(58) Field of Classification Search
CPC ........ G06Q 40/00; G06Q 40/08; G06Q 10/06; G06F 40/103; G06F 16/907; G06F 16/90332
(Continued)

(56) References Cited

U.S. PATENT DOCUMENTS 7,337,121 B1 *  2/2008  Beinat ................... G16H 50/50
                                                        705/3
11,263,382 B1   3/2022  Sharzer et al.
(Continued)

OTHER PUBLICATIONS

Asuk, C. (2010). A data-mining based fraud detection system for health insurance companies (Order No. 28538921). Available from ProQuest Dissertations and Theses Professional. (2561962387). Retrieved from https://dialog.proquest.com/professional/docview/2561962387 ?accountid=131444 (Year: 2010).*

*Primary Examiner* — Hani M Kazimi
(74) *Attorney, Agent, or Firm* — Knobbe, Martens, Olson & Bear, LLP

(57) ABSTRACT

A computer-implemented method is provided to provide analysis of claim information. The system may receive claim data from a plurality of entities and, for one or more claim items in the received claim data, determine a format of the claim item. The system may convert the claim item from the (Continued)

determined format into a standard format. The system may receive a selection of one or more providers, and determine one or more claim items associated with the provider in the selection. The system may generate a user interface, the user interface comprising a visual representation of one or more attributes of the one or more claim items.

16 Claims, 11 Drawing Sheets

Related U.S. Application Data

(60) Provisional application No. 62/610,039, filed on Dec. 22, 2017.

(51) Int. Cl.
*G06F 16/9032* (2019.01)
*G06F 16/907* (2019.01)
*G06F 17/18* (2006.01)
*G06F 40/103* (2020.01)
*G06Q 20/40* (2012.01)
*H04W 12/12* (2021.01)

(52) U.S. Cl.
CPC ............ *G06F 16/907* (2019.01); *G06F 17/18* (2013.01); *G06Q 20/4016* (2013.01); *H04W 12/12* (2013.01)

(58) Field of Classification Search
USPC .............................................. 705/4
See application file for complete search history.

(56) References Cited

U.S. PATENT DOCUMENTS

| | | | |
|---|---|---|---|
| 2006/0085221 A1* | 4/2006 | Lipsky | G06Q 10/10 705/2 |
| 2007/0260571 A1* | 11/2007 | Mansfield | G06F 40/154 706/48 |
| 2009/0106053 A1* | 4/2009 | Walker | G06Q 40/125 705/4 |
| 2010/0179838 A1* | 7/2010 | Basant | G16H 50/20 705/4 |
| 2010/0211413 A1* | 8/2010 | Tholl | G06Q 10/00 705/4 |
| 2011/0246229 A1* | 10/2011 | Pacha | G06Q 10/10 705/2 |
| 2012/0029950 A1* | 2/2012 | Lyle | G06Q 10/10 705/4 |
| 2012/0173289 A1* | 7/2012 | Pollard | G06Q 40/08 707/812 |
| 2012/0185275 A1* | 7/2012 | Loghmani | G06Q 40/08 705/3 |
| 2015/0088560 A1* | 3/2015 | DiRienzo | G06Q 40/08 705/4 |
| 2017/0270613 A1* | 9/2017 | Scott | G06Q 40/08 |
| 2021/0201423 A1* | 7/2021 | Speranza | G06Q 10/10 |

* cited by examiner

FRAUD FINDER

MY DATA

| Claim ID | Patient Name | Referrer | Patient Date of Birth | Patient Age | Referring Provider Name | Claim Date From | Claim Date To |
|---|---|---|---|---|---|---|---|
| 12345 | Eric Bell | Cyber Medical Care | 10/24/1975 | 42 | Karen Alcantara | 3/18/2011 | 3/25/2011 |
| 12346 | Eric Bell | Cyber Medical Care | 10/24/1975 | 42 | Karen Alcantara | 3/19/2011 | 3/26/2011 |
| 12347 | Eric Bell | Cyber Medical Care | 10/24/1975 | 42 | Karen Alcantara | 3/20/2011 | 3/27/2011 |
| 12348 | Eric Bell | Cyber Medical Care | 10/24/1975 | 42 | Karen Alcantara | 3/21/2011 | 3/28/2011 |
| 12349 | Eric Bell | Cyber Medical Care | 10/24/1975 | 42 | Karen Alcantara | 3/22/2011 | 3/29/2011 |
| 12350 | Eric Bell | Cyber Medical Care | 10/24/1975 | 42 | Karen Alcantara | 3/23/2011 | 3/30/2011 |
| 12351 | Eric Bell | Cyber Medical Care | 10/24/1975 | 42 | Karen Alcantara | 3/24/2011 | 3/31/2011 |
| 12352 | Eric Bell | Cyber Medical Care | 10/24/1975 | 42 | Karen Alcantara | 6/10/2011 | 6/23/2011 |
| 12353 | Eric Bell | Cyber Medical Care | 10/24/1975 | 42 | Karen Alcantara | 6/11/2011 | 6/24/2011 |
| 12354 | Eric Bell | Cyber Medical Care | 10/24/1975 | 42 | Karen Alcantara | 6/12/2011 | 6/25/2011 |
| 12355 | Eric Bell | Cyber Medical Care | 10/24/1975 | 42 | Karen Alcantara | 6/13/2011 | 6/26/2011 |
| 12356 | Eric Bell | Cyber Medical Care | 10/24/1975 | 42 | Karen Alcantara | 6/14/2011 | 6/27/2011 |
| 12357 | Eric Bell | Cyber Medical Care | 10/24/1975 | 42 | Karen Alcantara | 6/15/2011 | 6/28/2011 |
| 12358 | Eric Bell | Cyber Medical Care | 10/24/1975 | 42 | Karen Alcantara | 6/16/2011 | 6/29/2011 |
| 12359 | Tony Lee | Space Hall Health Care | 5/13/1950 | 67 | Karen Alcantara | 6/17/2011 | 6/30/2011 |
| 12360 | Tony Lee | Space Hall Health Care | 5/13/1950 | 67 | Karen Alcantara | 6/18/2011 | 7/1/2011 |
| 12361 | Tony Lee | Space Hall Health Care | 5/13/1950 | 67 | Karen Alcantara | 6/19/2011 | 7/2/2011 |
| 12362 | Tony Lee | Space Hall Health Care | 5/13/1950 | 67 | Karen Alcantara | 6/20/2011 | 7/3/2011 |
| 12363 | Tony Lee | Space Hall Health Care | 5/13/1950 | 67 | Karen Alcantara | 6/21/2011 | 7/4/2011 |
| 12364 | Tony Lee | Space Hall Health Care | 5/13/1950 | 67 | Karen Alcantara | 6/22/2011 | 7/5/2011 |
| 12365 | Tony Lee | Space Hall Health Care | 5/13/1950 | 67 | Karen Alcantara | 11/20/2011 | 11/30/2011 |
| 12366 | Tony Lee | Space Hall Health Care | 5/13/1950 | 67 | Karen Alcantara | 11/21/2011 | 12/1/2011 |
| 12367 | Tony Lee | Space Hall Health Care | 5/13/1950 | 67 | Karen Alcantara | 11/22/2011 | 12/2/2011 |
| 12368 | Tony Lee | Space Hall Health Care | 5/13/1950 | 67 | Karen Alcantara | 11/23/2011 | 12/3/2011 |
| 12369 | Tony Lee | Space Hall Health Care | 5/13/1950 | 67 | Karen Alcantara | 11/24/2011 | 12/4/2011 |
| 12370 | Tony Lee | Space Hall Health Care | 5/13/1950 | 67 | Karen Alcantara | 11/25/2011 | 12/5/2011 |
| 12371 | Tony Lee | Space Hall Health Care | 5/13/1950 | 67 | Karen Alcantara | 11/26/2011 | 12/6/2011 |
| 12372 | Tony Lee | Space Hall Health Care | 5/13/1950 | 67 | Karen Alcantara | 11/27/2011 | 12/7/2011 |
| 12373 | Tony Lee | Space Hall Health Care | 5/13/1950 | 67 | Karen Alcantara | 11/28/2011 | 12/8/2011 |
| 12374 | Tony Lee | Space Hall Health Care | 5/13/1950 | 67 | Karen Alcantara | 11/29/2011 | 12/9/2011 |

Amount Paid: 5, 2000, 3000, 5000

REFERENCE NAME
Karen Alcantara

PATIENT NAME
Eric Bell
Tony Lee
Jessica Rabbit

Referrers
Cyber Medical Care
Space Hall Health Care

Diagnoses
Cancer
Diabetes
Halitosis

FILE TYPE MAPPER

CHOOSE A TRANSFORMATION TEMPLATE ▶

| WILDLIFE TRACKING DATA ▶ |

- ANIMAL NAME
- ANIMAL SPECIES
- DATE/TIME
- DEPTH (M)
- LOCATION
- TRANSMITTER ID

| SELECT DATA FIELD ▶ | SELECT DATA FIELD ▶ | SELECT DATA FIELD ▶ | SELECT DATA FIELD ▶ | SELECT DATA FIELD ▶ |
|---|---|---|---|---|
| DATE | ON/OFF | TIME (UTC) | LAT (N) | LONG (W) |
| 5/3/00 | OFF | 2155 | 4203.9 | 6940.1 |
| 5/5/00 | OFF | 1330 | 4116.6 | 4264.1 |

FIG. 7D

DATA NORMALIZATION AND IRREGULARITY DETECTION SYSTEM

INCORPORATION BY REFERENCE TO ANY RELATED APPLICATIONS

This application is a continuation of U.S. patent application Ser. No. 15/873,753 entitled "Data Normalization and Irregularity Detection System" filed Jan. 17, 2018, which claims benefit of U.S. Provisional Patent Application Ser. No. 62/610,039 entitled "Data Normalization and Irregularity Detection System" filed Dec. 22, 2017. Each of these applications are hereby incorporated by reference in their entireties.

Any and all applications for which a foreign or domestic priority claim is identified in the Application Data Sheet as filed with the present application are hereby incorporated by reference under 37 CFR 1.57 for all purposes and for all that they contain.

TECHNICAL FIELD

Embodiments of the present disclosure relate to systems and techniques for accessing one or more databases and providing user interfaces for dynamic detection of irregularities.

BACKGROUND

Computer databases are being used to facilitate and audit various types of operations and transactions. Systems operating on such databases may be used to detect irregularities in the data.

SUMMARY

The systems, methods, and devices described herein each have several aspects, no single one of which is solely responsible for its desirable attributes. Without limiting the scope of this disclosure, several non-limiting features will now be described briefly.

Irregularity detection (e.g. detection of fraud or other anomalous phenomena) requires analysis of large datasets. In certain industries, such as the insurance industry, enormous amounts of data are being processed for payment and/or reimbursement. Not only is the data voluminous, but it has velocity and variability as well. Tens of thousands of claims or transactional records are being processed daily or even hourly; sometimes the volume can reach into the hundreds of thousands and millions. There are usually various data sources, each with its own format, codes, column headers, etc. Because individual review of the data items comprising such large and variable datasets may not be feasible or provide a complete picture of anomalies, generation of aggregate representations may be useful. Irregularity detection may be further complicated by heterogeneous data formats that also may include industry-specific codes and terminology. Embodiments of the present disclosure may be configured to receive and process data from various sources for irregularity detection. In some embodiments, the irregularity detection may be performed on claim data (e.g. reimbursement claim data submitted to benefit managers). To allow for analysis of data from heterogeneous sources (e.g. different sources of claim data, or providers), data from multiple entities and providers may be ingested and aggregated into a database. Different data formats may be standardized; specifically, codes or synonymous descriptions for various services from providers (e.g. automotive repairs, shipments of goods) may be translated, dereferenced or resolved into a uniform classification scheme. Data from different data sources may comprise codes, industry-specific terminology, abbreviations and informal verbiage that may make comprehension more difficult. Codes and industry-specific natural language may be translated, dereferenced, resolved, annotated or associated with a description to facilitate understanding by analysts without industry-specific knowledge by the system. Data formats provided by different providers and entities may be classified (e.g. based on file headers), associated with a schema or template that was previously seen, and processed accordingly. Different goods or services provided may be categorized based on common types (e.g. vehicle repair, vehicle towing, vehicle storage) and filtered and processed accordingly. Different providers may be aggregated based on common features or attributes, such as being located in a specific geographic area or being associated with a certain type of good or service provided. Claim data may comprise significant amounts of data items (e.g. in the hundreds of thousands, millions or billions ranges). As such, automated, aggregated and batch processing for irregularity and fraud detection becomes necessary.

Accordingly, in various embodiments, large amounts of data are automatically and dynamically calculated interactively in response to user inputs, and the calculated data is efficiently and compactly presented to a user by the system. In order to be effectively visualized, the data must be normalized or standardized. A backend user interface for data integration and normalization is disclosed. A frontend user interface allows for interactive manipulation of the data by a human analyst in order to detect unusual trends and/or irregularities which may comprise actual fraud. Thus, in some embodiments, the user interfaces described herein are more efficient as compared to previous user interfaces in which data is not dynamically updated and compactly and efficiently presented to the user in response to interactive inputs.

Visualizations may be created based on claim or transaction history by provider, group of providers or other parties to and types of transactions in question. Such visualizations may assist in detecting patterns of fraudulent claims by uncovering relationships and aggregating information wherein each item of information taken by itself may be insufficient to determine a claim as fraudulent. Visualizations may be chosen specifically to uncover typical fraud schemes or patterns associated with such schemes. For example, a chart of claim volume associated with a specific provider against time may assist in determining whether that provider is associated with fraudulent claims. Automatic generation of various measures of central tendency (e.g. median, mode, mean) and comparison of individual providers, groups of providers, claimants, groups of claimants, etc. against associated measures of central tendency may facilitate detection of various fraudulent schemes.

Further, as described herein, the system may be configured and/or designed to transform diverse data sources to make the data useable for rendering the various interactive user interfaces described. The user interface data may be used by the system, and/or another computer system, device, and/or software program (for example, a browser program), to render the interactive user interfaces. The interactive user interfaces may be displayed on, for example, electronic displays (including, for example, touch-enabled displays).

Additionally, it has been noted that design of computer user interfaces "that are useable and easily learned by humans is a non-trivial problem for software developers." (Dillon, A. (2003) User Interface Design. MacMillan Encyclopedia of Cognitive Science, Vol. 4, London: MacMillan, 453-458.) The various embodiments of interactive and dynamic user interfaces of the present disclosure are the result of significant research, development, improvement, iteration, and testing. This non-trivial development has resulted in the user interfaces described herein which may provide significant cognitive and ergonomic efficiencies and advantages over previous systems. The interactive and dynamic user interfaces include improved human-computer interactions that may provide reduced mental workloads, improved decision-making, reduced work stress, and/or the like, for a user. For example, user interaction with the interactive user interfaces described herein may provide an optimized interface for creating and scheduling data pipelines, and may reduce the complexity that a user setting up such data pipelines is exposed to.

Further, the interactive and dynamic user interfaces described herein are enabled by innovations in efficient interactions between the user interfaces and underlying systems and components. For example, disclosed herein are improved methods of receiving user inputs, translation and delivery of those inputs to various system components, automatic and dynamic execution of complex processes in response to the input delivery, automatic interaction among various components and processes of the system, and automatic and dynamic updating of the user interfaces. The interactions and presentation of data via the interactive user interfaces described herein may accordingly provide cognitive and ergonomic efficiencies and advantages over previous systems.

Various embodiments of the present disclosure provide improvements to various technologies and technological fields. For example, as described above, existing technologies for analyzing aggregate probabilities are limited in various ways (e.g., they are slow and cumbersome, they require more resources than can practically be made available, etc.), and various embodiments of the disclosure provide significant improvements over such technology. Additionally, various embodiments of the present disclosure are inextricably tied to computer technology. In particular, various embodiments rely on detection of user inputs via graphical user interfaces, automatic and/or self-learning data ingestion from a variety of different formats, calculation of statistical quantities associated with vast datasets (e.g. claim datasets comprising hundreds of thousands, millions or billions of data items). Such features and others (e.g., automated display of statistical quantities, such as means, medians and modes, associated with a dataset) are intimately tied to, and enabled by, computer technology, and would not exist except for computer technology. For example, the interactions with displayed data described below in reference to various embodiments cannot reasonably be performed by humans alone, without the computer technology upon which they are implemented. Further, the implementation of the various embodiments of the present disclosure via computer technology enables many of the advantages described herein, including more efficient interaction with, and presentation of, various types of data pipelines.

Additional embodiments of the disclosure are described below in reference to the appended claims, which may serve as an additional summary of the disclosure.

In various embodiments, systems and/or computer systems are disclosed that comprise a computer readable storage medium having program instructions embodied therewith, and one or more processors configured to execute the program instructions to cause the one or more processors to perform operations comprising one or more aspects of the above- and/or below-described embodiments (including one or more aspects of the appended claims).

In various embodiments, computer-implemented methods are disclosed in which, by one or more processors executing program instructions, one or more aspects of the above- and/or below-described embodiments (including one or more aspects of the appended claims) are implemented and/or performed.

In various embodiments, computer program products comprising a computer readable storage medium are disclosed, wherein the computer readable storage medium has program instructions embodied therewith, the program instructions executable by one or more processors to cause the one or more processors to perform operations comprising one or more aspects of the above- and/or below-described embodiments (including one or more aspects of the appended claims).

BRIEF DESCRIPTION OF THE DRAWINGS

FIGS. 3, 4, 5, and 6 are example user interfaces of an irregularity detection system.

FIGS. 7A-7D are example user interfaces of a data ingestion system.

DETAILED DESCRIPTION

Figure 1:
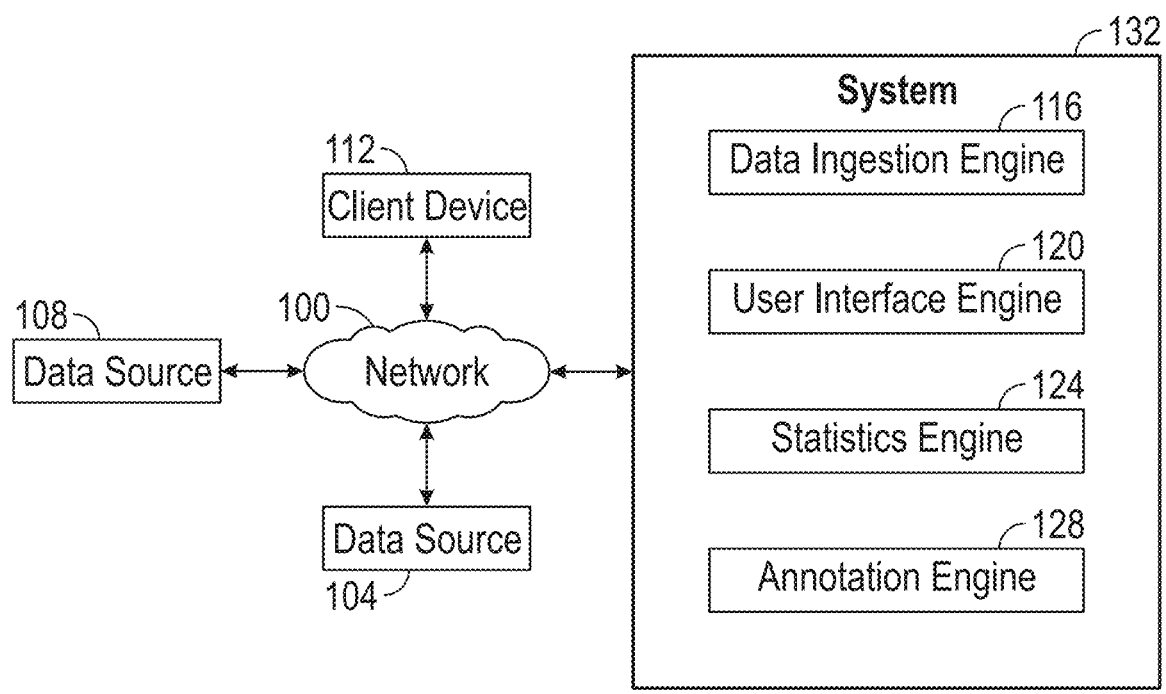
FIG. 1 is a block diagram illustrating an example irregularity detection system in an example operating environment.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Overview

Embodiments of the disclosure will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the disclosure. Furthermore, embodiments of the disclosure may include several novel features, no single one of which is solely responsible for its desirable attributes or which is essential to practicing the embodiments of the disclosure herein described.

Terms

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

User Input (also referred to as "Input"): Any interaction, data, indication, etc., received by the system from a user, a representative of a user, an entity associated with a user, and/or any other entity. Inputs may include any interactions that are intended to be received and/or stored by the system; to cause the system to access and/or store data items; to cause the system to analyze, integrate, and/or otherwise use data items; to cause the system to update to data that is displayed; to cause the system to update a way that data is displayed; and/or the like. Non-limiting examples of user inputs include keyboard inputs, mouse inputs, digital pen inputs, voice inputs, finger touch inputs (e.g., via touch sensitive display), gesture inputs (e.g., hand movements, finger movements, arm movements, movements of any other appendage, and/or body movements), and/or the like. Additionally, user inputs to the system may include inputs via tools and/or other objects manipulated by the user. For example, the user may move an object, such as a tool, stylus, or wand, to provide inputs. Further, user inputs may include motion, position, rotation, angle, alignment, orientation, configuration (e.g., fist, hand flat, one finger extended, etc.), and/or the like. For example, user inputs may comprise a position, orientation, and/or motion of a hand or other appendage, a body, a 3D mouse, and/or the like.

Data Store: Any computer readable storage medium and/or device (or collection of data storage mediums and/or devices). Examples of data stores include, but are not limited to, optical disks (e.g., CD-ROM, DVD-ROM, etc.), magnetic disks (e.g., hard disks, floppy disks, etc.), memory circuits (e.g., solid state drives, random-access memory (RAM), etc.), and/or the like. Another example of a data store is a hosted storage environment that includes a collection of physical data storage devices that may be remotely accessible and may be rapidly provisioned as needed (commonly referred to as "cloud" storage).

Database: Any data structure (and/or combinations of multiple data structures) for storing and/or organizing data, including, but not limited to, relational databases (e.g., Oracle databases, MySQL databases, etc.), non-relational and/or schema-free databases (e.g., NoSQL databases, etc.), in-memory databases, spreadsheets, as comma separated values (CSV) files, eXtendible markup language (XML) files, JSON (JavaScript object notation) files, TeXT (TXT) files, flat files, spreadsheet files, and/or any other widely used or proprietary format for data storage. Databases are typically stored in one or more data stores. Accordingly, each database referred to herein (e.g., in the description herein and/or the figures of the present application) is to be understood as being stored in one or more data stores.

Irregularity: A transaction or subset of information that deviates from a defined set of standard or rules (e.g., predefined rules, statistical expectations, or the like) or an expected type of behavior. In the context of business transactions, irregularity may be defined as a deviation from an agreed-upon or expected behavior (e.g., fraud).

Claim: Request for financial benefit or reimbursement, e.g., under a warranty contract or insurance plan Entity: Person or organization against which claims are made, or designated to make decisions on claims Provider: Person or organization providing a good or service associated with a claim.

Example Computing Devices and Systems

FIG. 1 illustrates an example processing system 132 in an example operational environment. Example processing system 132 may consist of a data ingestion engine 116, a user interface engine 120, a statistics engine 124 and an annotation engine 128. The components of processing system 132 may be interconnected by a variety of means, such as network connections, shared memory, named or anonymous pipes, etc., and may thus interact with each other. System 132 may be connected, for example via network 100, to one or more data sources, such as data source 104, and data source 108, and one or more client devices, such as client device 112. Network 100 may be any type of data network, such as, for example, the Internet, and Ethernet network, or a WiFi.

Data sources 104 and 108 may be type of automated, manual or semi-automated sources of information, such as transaction information. For example, data source 104 and/or data source 108 may be servers by providers. Data ingestion engine 116 may poll, for example, via network 100, the data sources, such as data source 108 and data source 104, so as to acquire, store and process the data provided by the data sources.

Data ingestion engine 116 may make the data from the data sources available for further processing and analysis, for example by storing them in a database, such as a relational or non-relational database, or a search engine. For example, data ingestion engine 116 may receive data from data source 104, and may store the data received in a table associated with data source 104 in a relational database. Event data may comprise various pieces of information associated with a transaction, such as, in the context of an insurance business, a type of claim, a time or date of the event giving rise to the claim, a provider associated with goods or services provided in connection with the claim, other parameters or observations, such as an amount, a location or a person or category associated with a claim, etc.

The data so acquired may then be used by other components of system 132, such as the statistics generation engine 124. and annotation engine 128. Annotation engine 128 may provide descriptive annotations of various elements associated with the data, thus augmenting the information received from the data sources with additional information.

The statistics engine 124 may process and analyze the data received from data sources, such as data source 104 and data source 108, to determine statistical quantities associated with the data items. Statistics engine 124 may, for example, calculate various measures of central tendency (e.g. median, mode, mean) and various measures of dispersion (e.g. variance, mean deviation, percentile).

System 132 may interact with a user through user interface engine 120. User interface engine 120 may be, for example, a web server, that accepts connections from a client device, such as client device 112, via network 100. User interface engine 120 may receive data from client device 112, and may store and/or forward it to the various other components of system 132. User interface engine 120 may also receive information from the other components of system 132, and send it, or present it, to the user through client device 112. Client device 112 may, for example, be an analyst's desktop computer, smartphone, or other type of computing device and associated software, e.g. a browser capable of rendering visual output from user interface engine 120's user interface data.

The data associated with data source 104 and data source 108 may be supplied directly from an entity (e.g. an insurance provider or service provider), e.g. via an Application Programming Interface (API) or request for information, or may be obtained by parsing or user interfaces provided by such an entity.

Figure 2:
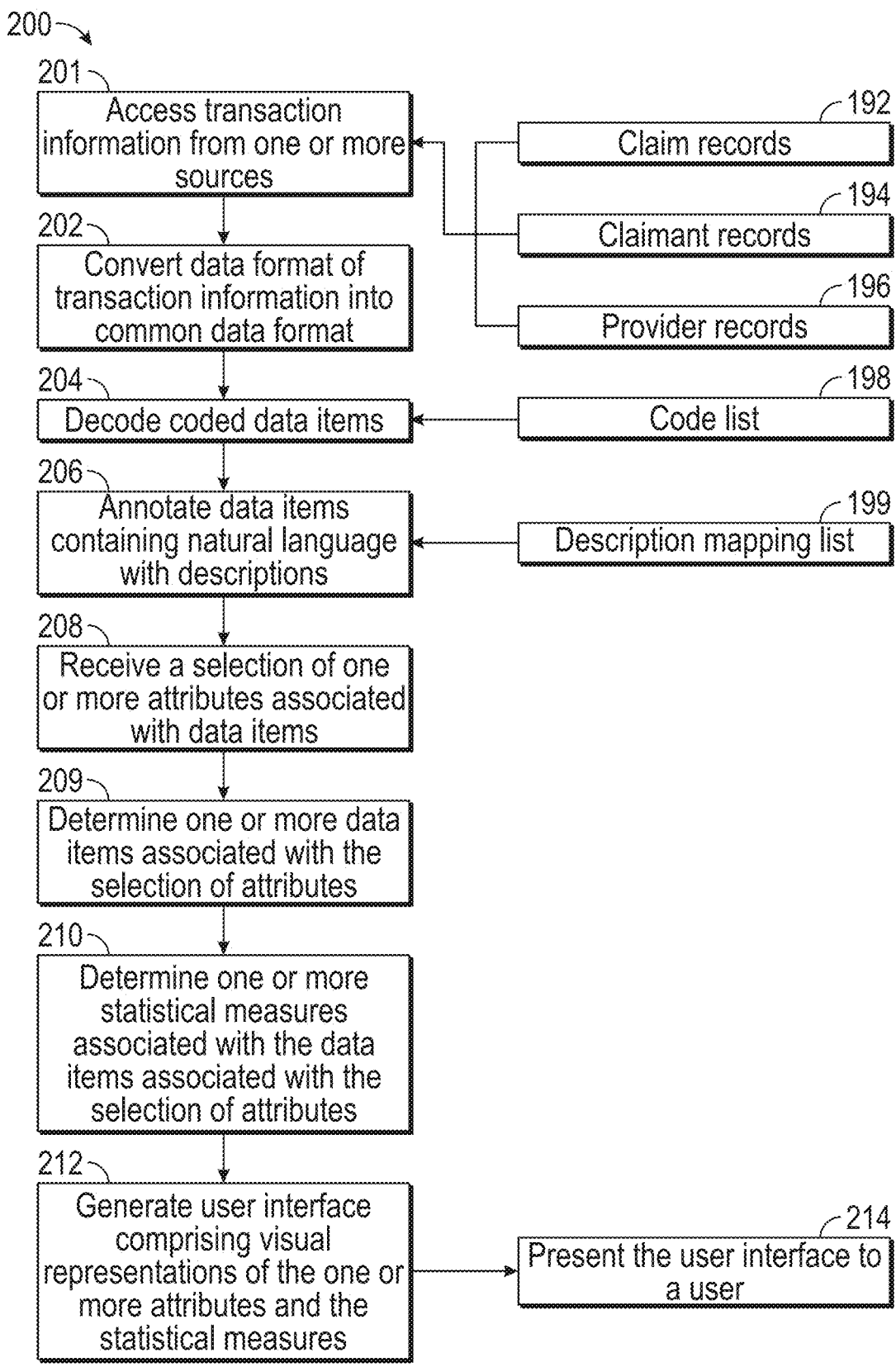
FIG. 2 is a flow chart illustrating an example method of acquiring, processing, and storing information, and detecting irregularities.

With reference now to FIG. 2, an example method 200 of acquiring, processing and presenting information related to irregularities is illustrated as a flow diagram.

In block 201, information such as transaction information may be received from one or more sources. The sources may include any type of database, record, ledger, log file, or other record of transaction information. For example, data sources utilized may include claim records 192, claimant records 194, and provider records 196. For example, in the context of vehicle insurance, claim records 192 may be associated with claims being made against the insurance company or carrier, claimant records 194 may include information about claimants and/or policy holders, such as personal information, demographic information, credit information, information about prior accidents, drivers' licenses, past traffic violations, etc. Provider records 196 may include information from various providers, such as the services and/or goods provided, the claimants to whom those services were provided, nonclaimants to whom those services were provided, the fees charged and actually collected from claimants and/or nonclaimants, etc.

In block 202, the information received in block 201 may be converted into a common data format. For example, each of claimant records 194 and/or provider records 196 may be in different formats (e.g., binary format, text format, relational database format, XML format, etc.). Additionally, the various records may comprise duplicate fields, missing fields, inconsistent fields, and other idiosyncrasies that may make direct comparisons difficult. The conversion process may be performed by detecting which format a given record or information item is associated with, and then running steps to transform the specific format into the common format. For example, the system may compare a data item against previously seen data items to determine whether the format is similar to a data format that was previously seen and/or processed. Advantageously, this may allow the system to learn or adapt to new formats as they become used, and thus over time increase the degree of automatization that can be accomplished during the data ingestion procedure. The conversion may be performed by data ingestion engine 116. To better allow a human data analyst to supervise and control the operation of data ingestion engine 116, data ingestion engine 116 may present user interfaces, such as discussed with reference to FIGS. 8A-8D. Advantageously, conversion into a common data format may include utilizing and/or combining the information received in block 201 with additional reference or comparison data. For example, in an instance where the information received in block 201 represents a prescription of a controlled substance (e.g. a painkiller drug), conversion into a common data format may include calculating a comparable or reference dose based on a common reference drug (e.g. daily opioid dose) for example by multiplying the ingredient strength, number of pills, and an equivalence factor (e.g. morphine milligram equivalent) and divide by the length of the prescription. This may allow different substances, delivery types and delivery schedules to be compared easily.

In block 204, any coded data items within the information, such as claim records 192, claimant records 194, or provider records 196, may be decoded or dereferenced, as appropriate. For example, transaction information may comprise coded references to, for example, services or goods provided by a provider. These codes and the associated meaning, such as a good or service provided, may be put into the system through a code list, such as code list 198. Code list 198 may contain associations or mappings between coded elements and their respective meaning or reference. For example, in the context of vehicle repair services, a code, such as "service 405" may be associated with a comprehensible name or description, such as "replace hydraulic fluids." The mappings in code list 198 may be standardized descriptions (e.g. imported from a reference table or entered by a user) or may be automatically generated by the system (e.g. by learning from existing data). For example, if a first dataset is provided that comprises both codes and descriptions, the system may infer the mapping and create a code list 198 based on it. If then a second dataset is provided that contains only codes, the descriptions may be automatically added from code list 198.

In block 206, the decoded and referenced data items may be annotated with descriptions or additional fields. For example, in instances where the information received in block 201 represents a drug prescription, additional fields may include a drug's generic name, strength, manufacturer, legislative classification, etc. Annotations may be provided both for data items that were decoded in a previous block such as block 204, as well as data items that comprise natural language. For example, with reference to the data item discussed above in the context of block 204, a description may be provided that explains the typical use of the repair performed, as well as a description of the process. Natural language pausing may also be used to associate data items with corresponding descriptions even where they are not coded. For example, the system may associate a data item referencing a procedure described as "ECU replacement" with a description of the associated procedure and the necessity by searching for, and annotating, text fragments, regular expressions, or other sequences within a natural language description. The association between text and natural language may be provided by a description mapping list 199; for example, description mapping list 199 may contain regular expressions, wildcard expressions, or other types of fuzzy-matched fragments, that are associated with natural language descriptions. For example, description mapping list 199 may provide a mapping between a regular expression, such as ".*(ECU|Engine Control Unit) *(ex)?chang.*", to a natural-language description, such as "Replacement of Engine Control Unit". Advantageously, the fuzzy matching of the regular expression captures various ways of describing the procedure, such as "ECU changed", "Engine Control Unit Change", or "ECU exchanged".

In block 208, a selection of one or more attributes of the data items may be received from a user. For example, the user may specify one or more providers, one or more claimants, one or more type of claims, one or more time periods, or other attributes associated with the data items. The selection of the attributes may be accomplished through an interactive user interface, such as may be provided by user interface server 150. The user may be presented, for example, with graphical user interface elements, such as sliders, text boxes, numerical spinners, dropdown selection boxes, text entry boxes, etc., as may be appropriate for the type of attribute to be specified. The user may also be able to use graphical or visual representations to specify some or more of the attributes, for example, by using a topographical map to specify providers within a certain geographical region, or by dragging, clicking, swiping, or performing other selection actions within a graph, chart, or other visual representation of data, to select a subset of such data. As another example, the user may be presented with a time series plot showing total claim volume over time. By selecting a certain region within the plot, the user may be able to filter or select data items within the selected subregion or subperiod.

In block 209, one or more data items may be determined that are associated with the selection of attributes. For example, data items may be selected if the claimant associated with the data item matches the claimant or claimants specified in block 208, for the provider associated with the data item matches the provider specified in block 208.

In block 210, the one or more data items associated with the selection of attributes as determined in block 209 are further analyzed to determine one or more statistical measures. The statistical measures may include measures of central tendency, such as mean, median, or mode; they may also include measures of dispersion, such as variants, standard deviation, percentiles, such as $75^{th}$, $80^{th}$, $90^{th}$, $95^{th}$, or $98^{th}$ percentile, or any other measure of dispersion. They may also include measures of cross-correlation or auto-correlation; for example, the system may calculate across correlation matrix between one or more sets of data items or one or more attributes of the data items.

In block 212, a user interface is generated comprising visual representations of the one or more attributes, as selected in block 208, and the statistical measures, as determined in block 210. The visual representations may include a graph, plot or chart, or any other type of visualization of one or more attributes of the data items. For example, a graph may be generated that illustrates a time series plot of the one or more data items' statistical measures, broken down by time period. For example, the user may be shown a graph that illustrates the average claim volume per provider for each of the past 10 years of data.

In block 214, the user interface may be presented to the user.

Example User Interface of the Visualization System

Figure 3:
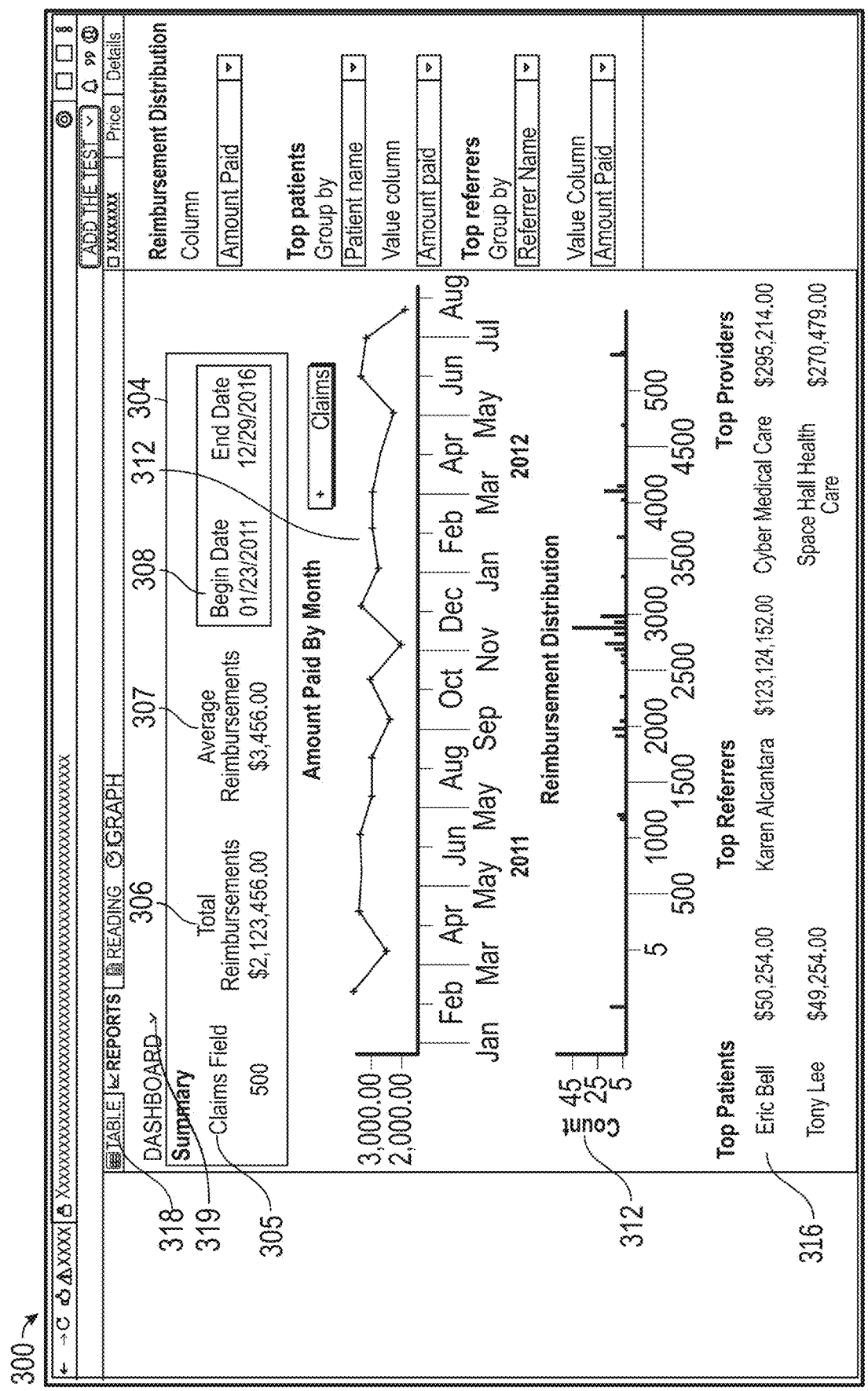

FIG. 3 illustrates an example user interface of an anomaly detection system, according to an embodiment. FIG. 3 illustrates an example user interface 300, comprising various elements including an overview panel 304, a time series graph 312, a distribution 312, and a histogram for fields of interest 316, and a drop-down indicator 319. Overview panel 304 comprises various statistical indicators such as a total amount of data items 305, a monetary total associated with all of the data items 306, an average monetary amount associated with the data items 307, and an indicator of the time period under consideration 303 (comprising, e.g. a beginning and end date). Advantageously, the statistical information associated with indicators 305, 306, and 307 (e.g. a total, an average, a mode from certain data items), may be calculated for data items associated with the time span shown in indicator 308. Graph 312 illustrates the total value associated with data items for each month within the time period associated with indicator 308. Chart 312 illustrates the distribution of values of data items associated with time period shown in indicator 308. Column 316 presents a histogram of various attributes, such as an amount paid, for fields of interest such as name of the claimant or name of a provider from the data items associated with time span 308. Advantageously, column 316 may show extreme values from the data items, such as a most frequent claimant, highest-grossing provider, etc. The data associated with the items presented in column 316 may be derived from statistics engine 124. The data presented may facilitate irregularity detection by displaying aggregate quantities and combined quantities, such as sum, count, mean, average, mode, most frequent item, etc. The reviewer is thus immediately directed to items of the dataset that may potentially be irregular without having to manually review each item (e.g. each claim, each provider). Additionally, by presenting the most frequent and/or most important (e.g. highest monetary value) data items, the reviewer's focus can be on irregularities having the greatest effect. User interface selector 318 may allow the user to review the data set in a different representation or format. By selecting a table view in user interface selector 318, the user may be presented with a table view, such as user interface 400 discussed herein. By selecting a graph view in user interface selector 318, the user may be presented with a graph view such as user interface 500 discussed herein. By selecting drop-down indicator 319, the user may be presented with a list or enumeration of other available views, such as user interface 400 and user interface 500.

Figure 5:
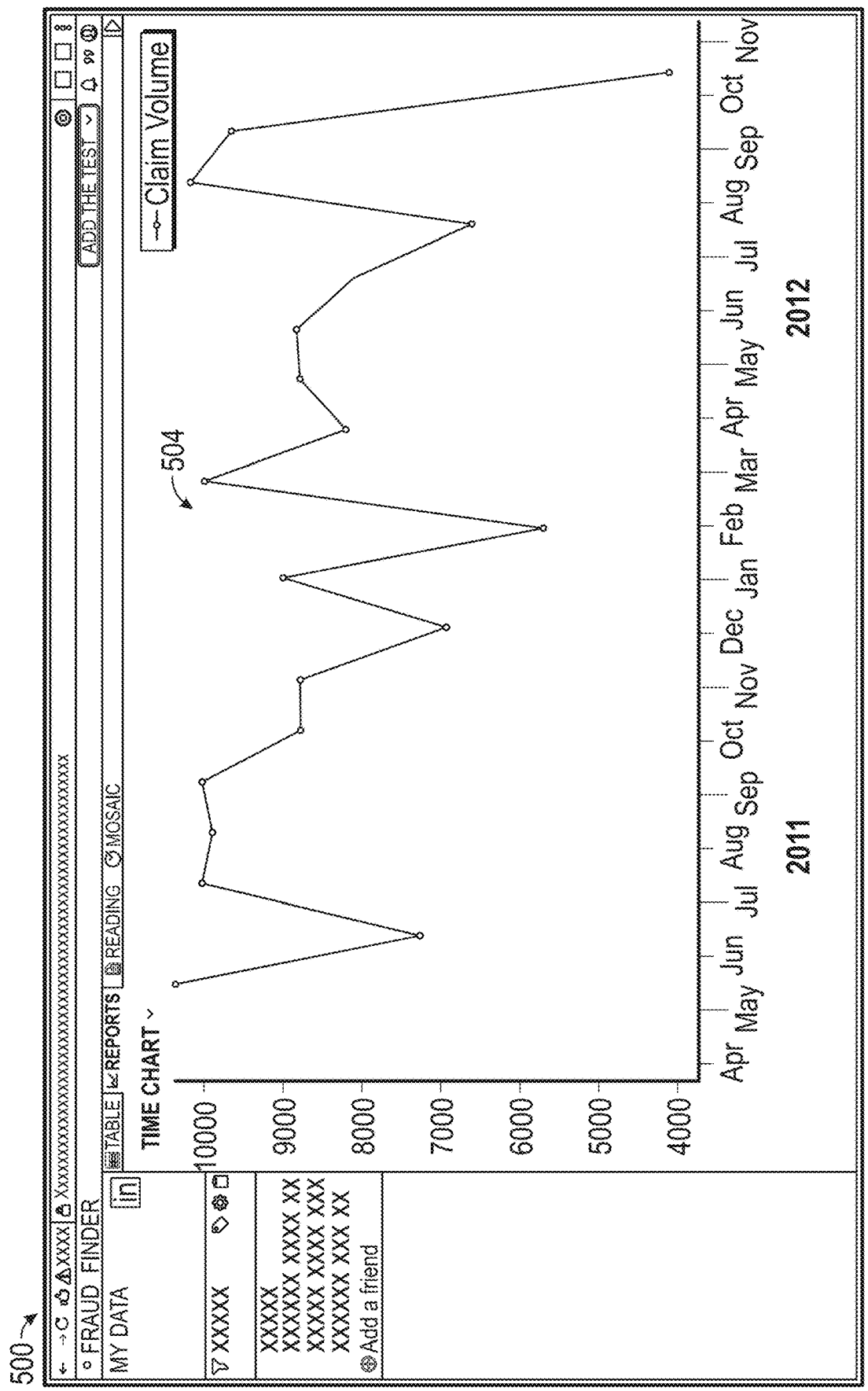
Figure 6:
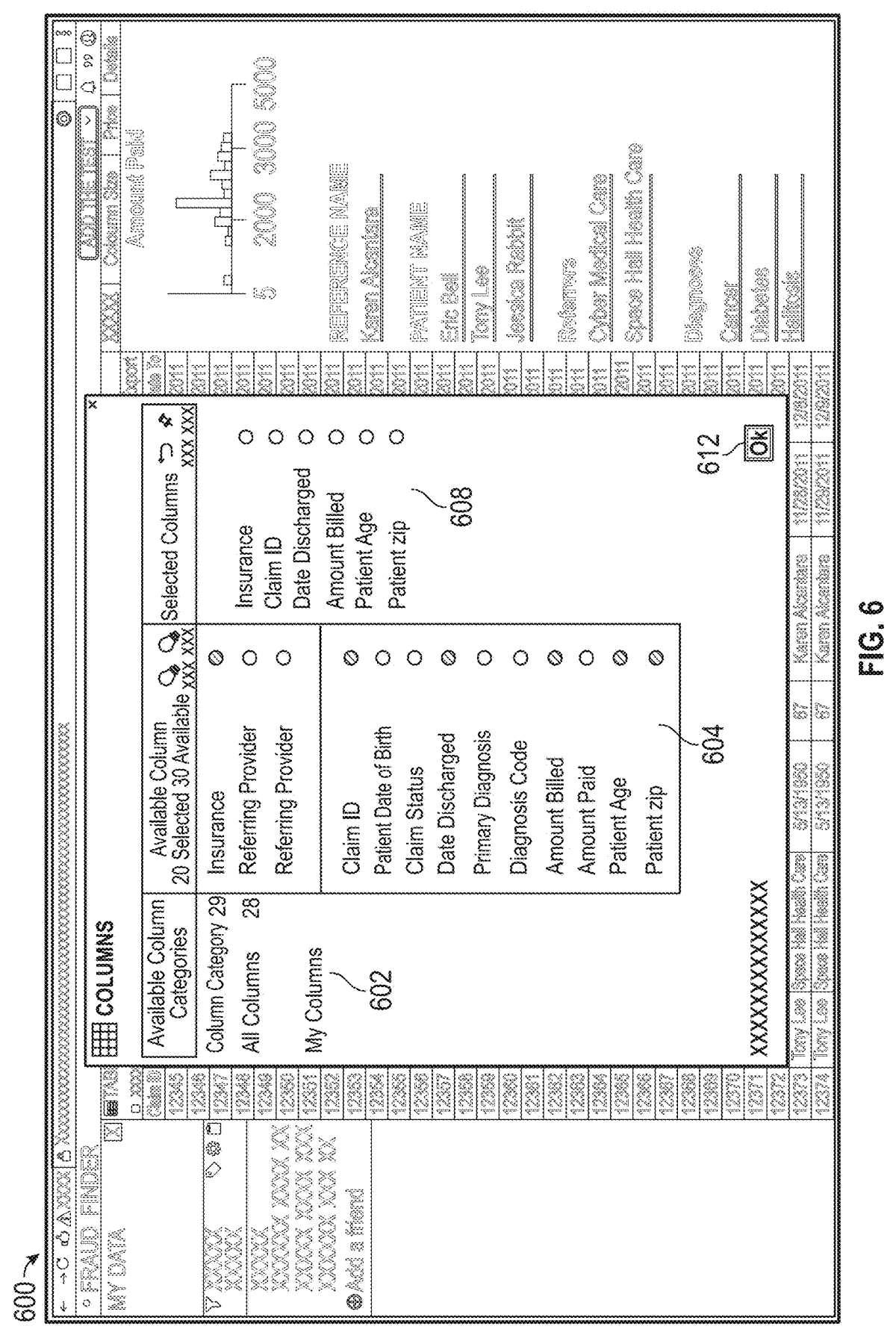

FIGS. 4, 5, 6 illustrate example user interfaces of a visualization system according to an embodiment. The Figures illustrate in brief form how a human analyst can use the present system to detect fraud by interactively manipulating the claims and payment data, as well as other attributes and indicators in the data. For example, in FIG. 4, large datasets which have been received from various different sources in different formats are aggregated in tabular format. From this view, various graphs and reports, such as the one illustrated in FIG. 5, can be generated to assist the analyst in detecting irregularities. It will be noted, in the right hand panel of FIG. 4, that the analyst can focus on certain attributes of the data that seem suspicious, such as the top claimants, referrers, or providers, as illustrated in FIG. 3. Because numerous data columns are created in the aggregated data, not all columns can be illustrated at once. For example, there may be dozens of available data columns that cannot be effectively visualized by a human analyst. Thus, only 8 columns are visible in FIG. 4. However, as shown in FIG. 6, the analyst is able to quickly and efficiently visualize different columns, for the same data attributes (claimants or patients, referrers, or providers) in order to continue the search for fraud. Thus, the details of these Figures will now be discussed.

FIG. 4 illustrates a table of an example user interface 400, illustrating various information in a table 402 associated with a filtering column 406. Table 402 may comprise various columns, including an ID column 402a, a claimant name column 402b, a provider column 402c, a claimant date of birth column 402d, a claimant age column 402e, a claimant referral column 402f, a claim date column 402g, and a claim date end column 402h. The information presented may be summarized in mode column 406. Mode column 406 may comprise a distribution 407 and relevant histograms 408. Histogram 408 may display a visual representation of selected data items shown in table 402; for example, indicator section may show most frequent claimants, most frequent providers, most frequent type of claims. Each indicator in indicator section 408 may comprise a label (e.g. name of the claimant, type of the claim), and a visual element (e.g. a bar or a circle), the dimension of which is associated with a frequency or magnitude of the associated element. For example, a longer bar or a more filled circle may represent a higher frequency or magnitude of the associated element. The information associated with indicator section 408 may be derived from statistics engine 124, and may be determined as a mode or a set of most frequently occurring elements in the dataset. The types and categories of data, such as statistical measures, presented may be chosen in an appropriate user interface, such as discussed herein with reference to FIG. 6.

FIG. 5 illustrates a time-series chart 504 of a statistical measure from the dataset, such as a total claim volume. As shown, interpolation (e.g. linear interpolation, Bezier splines, cubic interpolation, etc.) may be provided between data values to provide for continuous and smooth visual display. The graphing and interpolation may be provided by statistics engine 124.

FIG. 6 illustrates a user interface 600 providing a selection of attributes shown and/or statistical measures presented by the system, such as in FIGS. 5 and 6. In an available columns categories column 602, various categories of statistical measures or attributes may be listed. Upon selection of category in available categories column 602, columns associated with the selected category may be listed in available columns column 604. In a selected columns column 608, the types and categories of data currently chosen for presentation, visualization or analysis may be listed. Upon selection of one or more categories in available categories column 602, the selected categories may be moved or duplicated to selected columns column 608, and user interfaces 300, 400 and 500 refreshed or redrawn to encompass the newly selected categories. Similarly, upon selection of one or more categories in available categories in selected categories column 608, the selected categories may be removed from selected categories column 608 and the associated user interfaces. User interface 608 may be dismissed using confirmation button 612.

Advantageously, an analyst user may utilize user interface selector 318 to switch back and forth between various user interfaces, such as user interface 300, 400 and 500. The analyst user may, for example, review overview panel 304, graph 308 and histogram 312 to determine that, for example, an unusual uptick in overall claim volume has taken place that may have been partially driven by claims in amounts just between $2,500 and $3,000. Proceeding to user interface 500 using user interface selector 318, the analyst user is able to confirm the uptick in claim volume by reviewing graph 504. The analyst user is immediately able to spot the pattern because data is presented intuitively in user interface 300 and user interface 500. The analyst user may then utilize user interface selector 318 to proceed to user interface 400. The user can now scroll through the table to individually review the claims with the anomalous pattern. For example, the user may discover upon reviewing the various columns that the claims giving rise to the anomaly were submitted by a specific provider or referrer. Advantageously, because the user was presented with the graphical user interfaces, including user interfaces 300, 400 and 500, the user may arrive at this conclusion without reviewing a significant portion of the data and focus directly on the potentially significant data items.

FIGS. 7A-7D depict illustrations of an example GUI 700 as may be generated by a data ingestion system (e.g., data ingestion engine 116). As discussed herein, data ingestion engine 116 may utilize GUI 700 to request information from a user about data formats being provided to data ingestion engine 116, so as to facilitate the data ingestion process to system 132. This data ingestion process facilitates the transformation of data which is received in disparate data formats into a normalized or standardized data format, such as that shown in the table of FIG. 4. This data ingestion can be performed automatically by mapping templates or rules which transform the data into the desired format, or can be manually transformed using a data mapper user interface. Once a template for a given data source is created, it can be saved and used by the system in the future to automatically recognize the data source and transform it into the desired format.

Figure 7A:
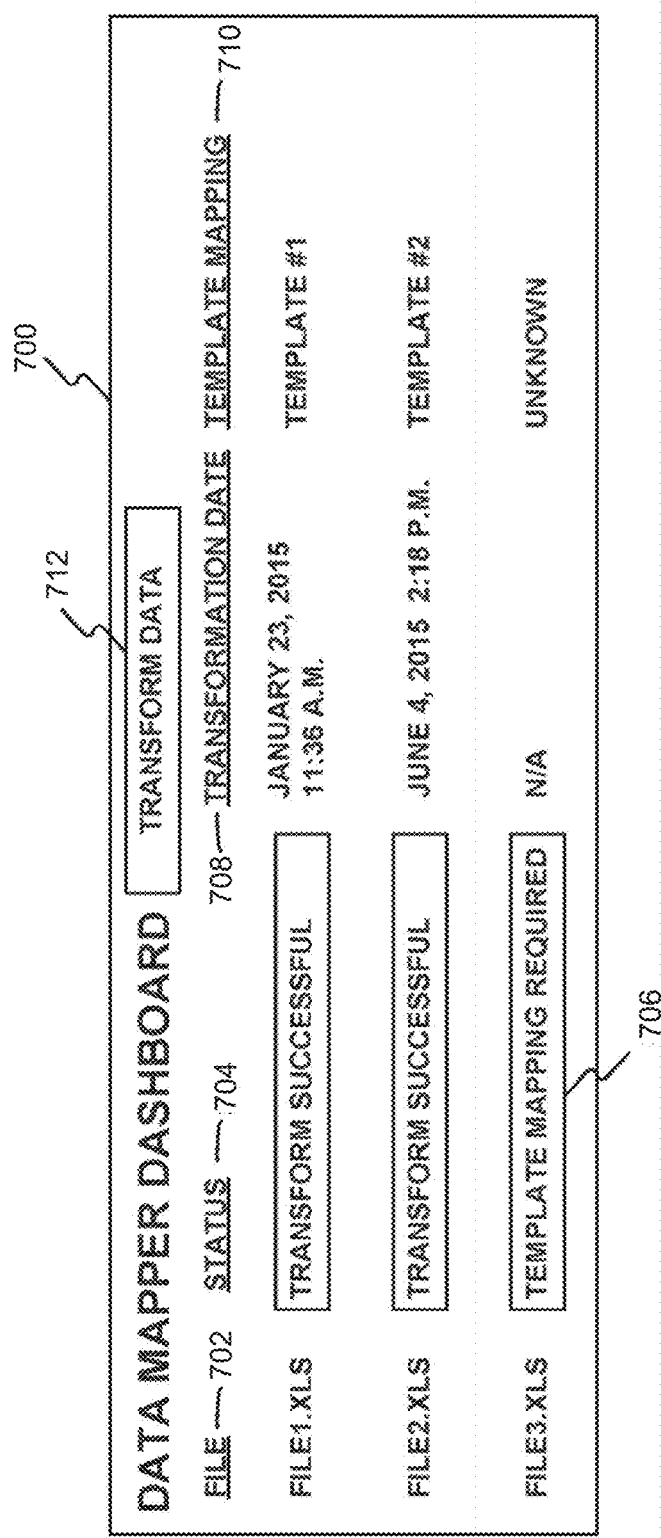

GUI 700 may be used to map electronic data files and to generate file type profiles, according to some embodiments of the present disclosure. FIG. 7A depicts a dashboard view of GUI 700. The dashboard view may display the status of various source electronic data files managed by the data importation system. The status of each source electronic data file may include a file name 702, transformation status 704, transformation date 708, and the template mapping 710 that is used to transform the source electronic data file. It is to be understood that the number of files illustrated in the example dashboard view of GUI 700 is merely an example and that any number of files may be displayed. Moreover, the dashboard view of GUI 700 may be configured to display subset of the files stored in the data importation system's source file database at one time. When a subset of the files is displayed, the dashboard view of GUI 700 allows the user to scroll through the list of source electronic data files stored in the source file database and to change the subset of files displayed.

Moreover, the dashboard view of GUI 700 may be configured to filter files stored in the source file database according to, for example, file type, file format, importation status, etc., in order to display a subset of the stored files.

File name 702 may list the file name and file format of each electronic data file stored in the data importation system's file database.

Transformation status 720 may list the importation status of each file.

In some embodiments, the transformation status 704 of each file may include an indicator 706 that indicates whether the data included in each file has been successfully transformed (i.e., transformed into a transformed source electronic data file). Indicator 706 may be a visual indicator that notifies the user of the data importation system that transformation of a given file was successful or that additional information is required in order to transform the file. Moreover, indicator 706 may be an interactive indicator that includes a hyperlink.

The data ingestion system may display a file type profile generator view in response to the user interacting with the hyperlink. It is to be understood that indicators 706 illustrated in FIG. 7A are merely an example and that indicators 706 may be, for example, a pop-up text box, a flag, an email message, an error report, or any visual indicators known in the art and combinations thereof.

Transformation date 708 may list the date that the transformation of a given file was completed successfully. For example, as shown in FIG. 7A, transformation date 708 may include the date and time of successful transformation of each file. In some embodiments, transformation date 708 may include only the date of successful transformation. In some embodiments, the date and/or time listed in transformation date 708 may be displayed in various formats such as, for example, date/time, time/date, in a "MM/DD/YY" date format, in a "Month Date, Year" date format, in 12-hour time format, in 24-hour time format, etc.

Template mapping 710 may list the transformation template that was used to transform the data in a given file. For example, template mapping 710 may display the name of the transformation template (e.g., weather buoy data) that was used to transform the data in a given file.

Transform data button 712 may include a graphical representation of a push button and an underlying hyperlink. The hyperlink, when interacted with by a user, may provide instructions to the data ingestion system to transform data included in one or more source electronic data files. In some embodiments, the data ingestion system may transform the data included in all source electronic data files stored in the source file database. For example, the data ingestion system may analyze each file to determine if there are any source electronic data files stored in the source file database that haven't yet been transformed. If the data ingestion system determines that a source electronic data file has already been transformed, the data ingestion system moves to the next file without retransforming that file. In some embodiments, the data ingestion system may transform data included in source electronic data file that have been selected by the user for transformation.

Figure 7B:
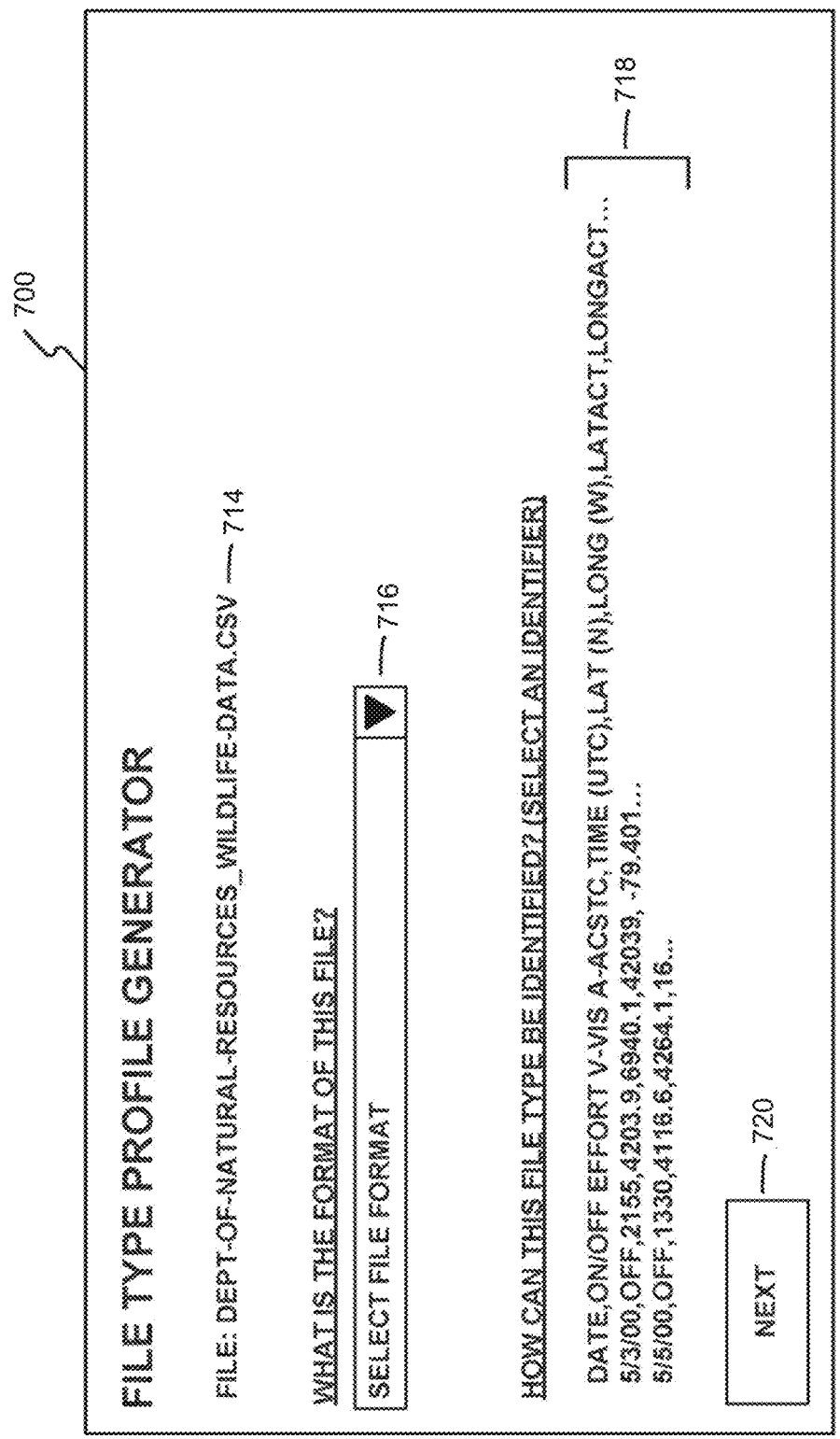

FIG. 7B, illustrates a file type profile generator view of GUI 700. In some embodiments, the file type profile generator view may be displayed in response to the user interacting with an underlying hyperlink of an indicator 706. The file type profiler generator view may display the file name 714 of the selected source electronic data file, a file format selector 716, content 718 included in the selected source electronic data, and a generator button 720 for initiating mapping of the file type associated with the selected source electronic data file to a transformation template.

Format selector 716 may allow the user to select a file format associated with the source electronic data file. As illustrated in FIG. 7B, format selector 716 may be implemented as a drop-down box that may expand to display a list of file formats selectable by the user. For example, the user may expand format selector 716 to select the .csv file format since the selected source electronic data file is a .csv file.

Content 718 may include a subset of the content included in the selected source electronic data file. For example, content 718 may include strings of text, column headers, data, or any other content included in the source electronic data file. In some embodiments, content 718 may be displayed so that the user can select a portion of content 718 that can be used by the data ingestion system to identify a file type associated with the selected source electronic data file. The user may select a portion of content 718 by highlighting combinations of data fields, headings, descriptions, data provider codes, and text strings included in content 718.

Once format selector 716 has received selection of the file format associated with the source electronic data file and the user has selected a portion of content 718, the user may select generator button 720 to continue with generating the file type profile. A file type mapper view of GUI 700 may be displayed in response to the user's selection of generator button 720.

Figure 7C:
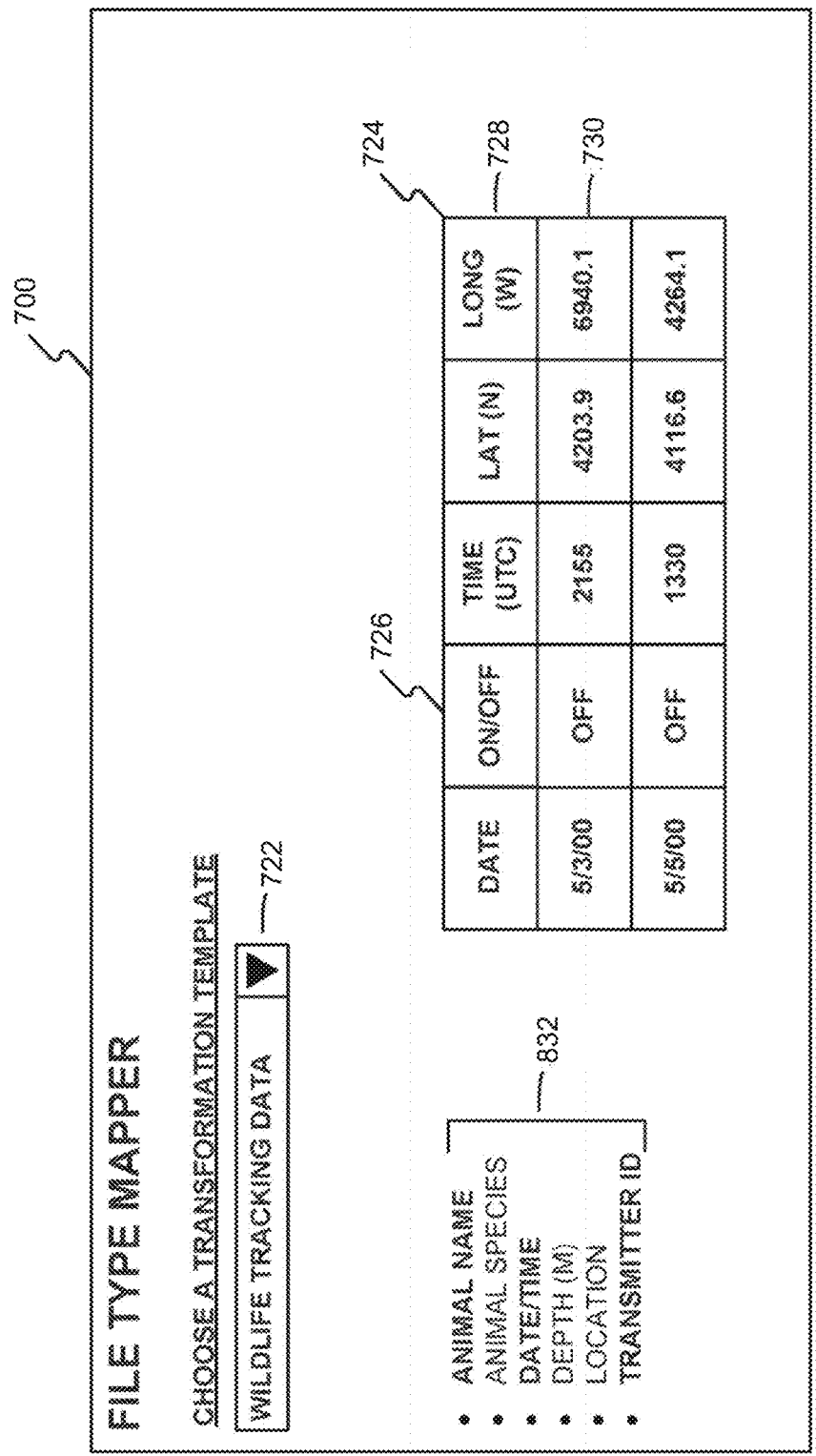

FIG. 7C illustrates an example file type mapper view of GUI 700, according to some embodiments of the present disclosure. As shown in FIG. 7C, the file type mapper view may include a transformation template selector 722 and content 724. Template selector 722 may allow the user to assign a transfer template to the file type profile being generated.

As illustrated in FIG. 7C, template selector 722 may be implemented as a drop-down box that may expand to display a list of transformation templates selectable by the user.

Content 724 may include content included in the selected source electronic data file. While content 724 is shown in FIG. 7C as being embedded in the file type mapper view of GUI 700, content 720 may instead be displayed in a native document viewer associated with selected source electronic data file (e.g., a spreadsheet viewer if the file is a spreadsheet) or in a separate a web page. As shown in FIG. 7C, content 724 may be displayed in a matrix format and include a plurality of data fields 726. Each data field 726 of the matrix may include a column header 728 and data 730.

The file type mapper view may display a list of canonical data fields 732 in response to receiving the user's selection of a transformation template at template selector 722. Canonical data fields 722 may include data fields required by the selected transformation template and data fields that are optional. Canonical data fields 722 may, for example, request information about an entity or software that has created the file, a type of data stored in the file, a source or provider (e.g. benefits manager) of the data contained in the file, etc. As illustrated in FIG. 7C, the required canonical data fields are visually distinguished from the optional canonical data fields by displaying the required data fields in bold text. Advantageously, some or all of canonical data fields 732 may be assigned automatically based on string or binary matching (e.g. fuzzy matching) between a column header 728, data 730 and/or additional metadata (e.g. a filename of an input file, a database, table or sheet name, etc.). For example, a regular expression (regex) may be applied by the system to match spreadsheet files containing sheets named "all claims". Upon matching the regular expression to the names of one or more sheets, the system may assign to those data fields in canonical data fields 722 associated with those sheets certain default or initial values (e.g. values indicating that the respective data is associated with claims).

As illustrated in FIG. 7D, file type mapper view of GUI 700 may also display drop-down boxes 734 above column headers 728. Each drop-down menu may include the list of canonical data fields 732 associated with selected transformation template. The user may map canonical data fields 732 to data fields 726 by selecting the canonical data field 732 from the drop-down menu that corresponds to each data field 726 of content 724.

In some embodiments, the system may provide automatic or manual updates or re-calculation of quantities, such as asset locations, and/or may provide alerts, e.g. in situations where an asset's position was not updated within a given period of time. Automatic updating may be triggered on a periodic schedule (e.g. daily, weekly, or monthly), or based on new data becoming available.

Updated information may be provided via notifications or reports that are automatically transmitted to a device operated by the user associated with a corresponding trigger. The report and/or notification can be transmitted at the time that the report and/or notification is generated or at some determined time after generation of the report and/or notification. When received by the device, the notification and/or reports can cause the device to display the notification and/or reports via the activation of an application on the device (e.g., a browser, a mobile application, etc.). For example, receipt of the notification and/or reports may automatically activate an application on the device, such as a messaging application (e.g., SMS or MMS messaging application), a standalone application (e.g., a designated report viewing application), or a browser, for example, and display information included in the report and/or notification. If the device is offline when the report and/or notification is transmitted, the application may be automatically activated when the device is online such that the report and/or notification is displayed. As another example, receipt of the report and/or notification may cause a browser to open and be redirected to a login page generated by the system so that the user can log in to the system and view the report and/or notification. Alternatively, the report and/or notification may include a URL of a webpage (or other online information) associated with the report and/or notification, such that when the device (e.g., a mobile device) receives the report, a browser (or other application) is automatically activated and the URL included in the report and/or notification is accessed via the Internet. In an embodiment, access to the report and/or notification may be controlled or restricted by an authentication scheme, for example to restrict access to authenticated users possessing a security clearance specific to the report and/or notification.

Additional Implementation Details and Embodiments

Various advantages may be provided by embodiments of the present disclosure. Anomalies in billing practices are often only detectable across various information sources and may thus be determined with higher accuracy and fewer information gaps than using any single source. Through programmatic normalization techniques, data sources in various formats can be standardized and utilized. Interactive user interfaces, such as the timeline, the indicators on the dashboard, and the interactive tables, allow the user to quickly filter the displayed information to locate fraud.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, Groovy, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure.

It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 8:
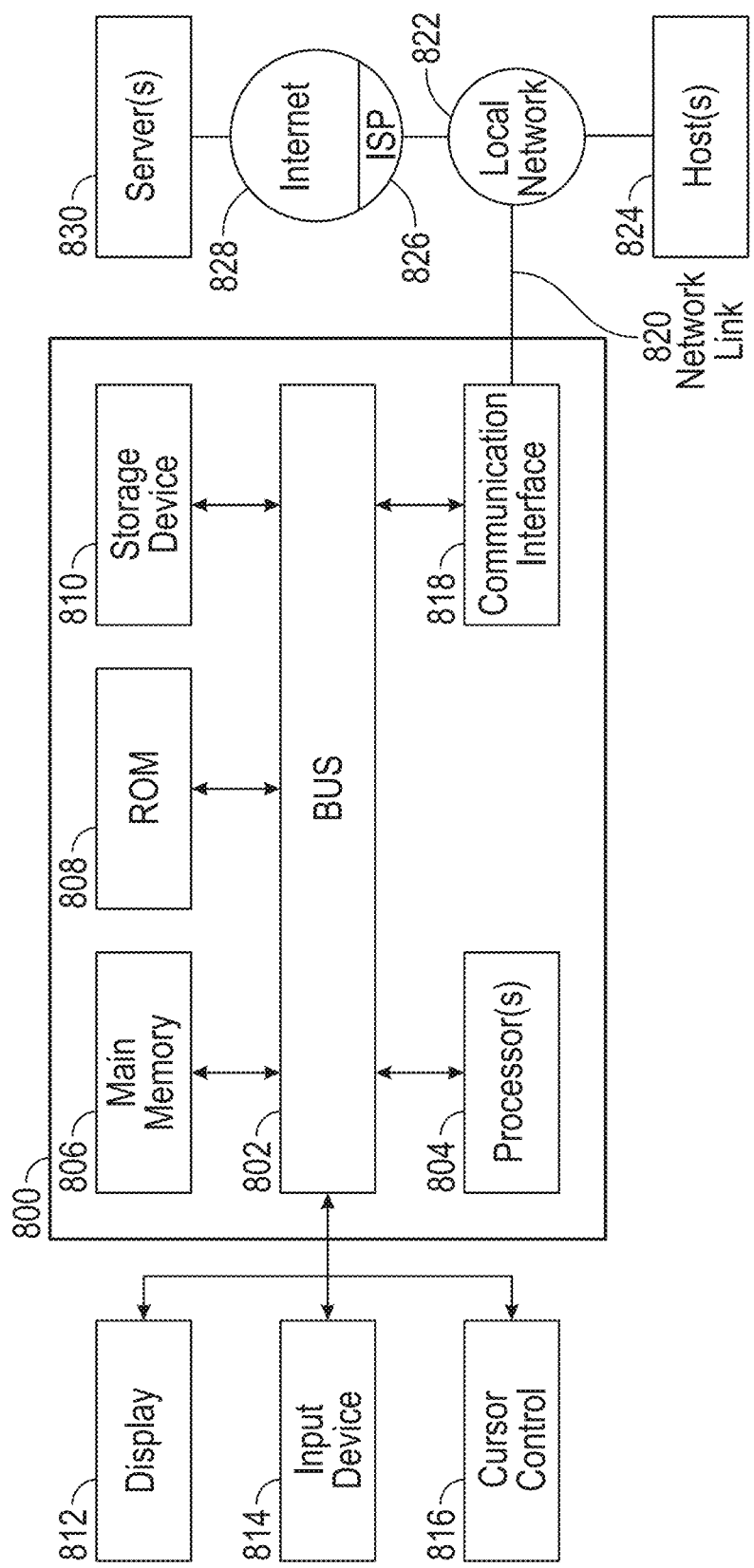
FIG. 8 illustrates an example computer system, with which certain methods discussed herein may be implemented.

For example, FIG. 8 is a block diagram that illustrates a computer system 800 upon which an embodiment may be implemented. Computer system 800 includes a bus 802 or other communication mechanism for communicating information, and a hardware processor, or multiple processors, 804 coupled with bus 802 for processing information. Hardware processor(s) 804 may be, for example, one or more general purpose microprocessors.

Computer system 800 also includes a main memory 806, such as a random access memory (RAM), cache and/or other dynamic storage devices, coupled to bus 802 for storing information and instructions to be executed by processor 804. Main memory 806 also may be used for storing temporary variables or other intermediate information during execution of instructions to be executed by processor 804. Such instructions, when stored in storage media accessible to processor 804, render computer system 800 into a special-purpose machine that is customized to perform the operations specified in the instructions.

Computer system 800 further includes a read only memory (ROM) 808 or other static storage device coupled to bus 802 for storing static information and instructions for processor 804. A storage device 810, such as a magnetic disk, optical disk, or USB thumb drive (Flash drive), etc., is provided and coupled to bus 802 for storing information and instructions.

Computer system 800 may be coupled via bus 802 to a display 812, such as a cathode ray tube (CRT) or LCD display (or touch screen), for displaying information to a computer user. An input device 814, including alphanumeric and other keys, is coupled to bus 802 for communicating information and command selections to processor 804. Another type of user input device is cursor control 816, such as a mouse, a trackball, or cursor direction keys for communicating direction information and command selections to processor 804 and for controlling cursor movement on display 812. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 800 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage Computer system 800 may implement the techniques described herein using customized hard-wired logic, one or more ASICs or FPGAs, firmware and/or program logic which in combination with the computer system causes or programs computer system 800 to be a special-purpose machine. According to one embodiment, the techniques herein are performed by computer system 800 in response to processor(s) 804 executing one or more sequences of one or more instructions contained in main memory 806. Such instructions may be read into main memory 806 from another storage medium, such as storage device 810. Execution of the sequences of instructions contained in main memory 806 causes processor(s) 804 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 810. Volatile media includes dynamic memory, such as main memory 806. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise bus 802. Transmission media can also take the form of acoustic or light waves, such as those generated during radio-wave and infra-red data communications.

Various forms of media may be involved in carrying one or more sequences of one or more instructions to processor 804 for execution. For example, the instructions may initially be carried on a magnetic disk or solid state drive of a remote computer. The remote computer can load the instructions into its dynamic memory and send the instructions over a telephone line using a modem. A modem local to computer system 800 can receive the data on the telephone line and use an infra-red transmitter to convert the data to an infra-red signal. An infra-red detector can receive the data carried in the infra-red signal and appropriate circuitry can place the data on bus 802. Bus 802 carries the data to main memory 806, from which processor 804 retrieves and executes the instructions. The instructions received by main memory 806 may retrieves and executes the instructions. The instructions received by main memory 806 may optionally be stored on storage device 810 either before or after execution by processor 804.

Computer system 800 also includes a communication interface 818 coupled to bus 802. Communication interface 818 provides a two-way data communication coupling to a network link 820 that is connected to a local network 822. For example, communication interface 818 may be an integrated services digital network (ISDN) card, cable modem, satellite modem, or a modem to provide a data communication connection to a corresponding type of telephone line. As another example, communication interface 818 may be a local area network (LAN) card to provide a data communication connection to a compatible LAN (or WAN component to communicated with a WAN). Wireless links may also be implemented. In any such implementation, communication interface 818 sends and receives electrical, electromagnetic or optical signals that carry digital data streams representing various types of information.

Network link 820 typically provides data communication through one or more networks to other data devices. For example, network link 820 may provide a connection through local network 822 to a host computer 824 or to data equipment operated by an Internet Service Provider (ISP) 826. ISP 826 in turn provides data communication services through the world wide packet data communication network now commonly referred to as the "Internet" 828. Local network 822 and Internet 828 both use electrical, electromagnetic or optical signals that carry digital data streams. The signals through the various networks and the signals on network link 820 and through communication interface 818, which carry the digital data to and from computer system 800, are example forms of transmission media.

Computer system 800 can send messages and receive data, including program code, through the network(s), network link 820 and communication interface 818. In the Internet example, a server 830 might transmit a requested code for an application program through Internet 828, ISP 826, local network 822 and communication interface 818.

The received code may be executed by processor 804 as it is received, and/or stored in storage device 810, or other non-volatile storage for later execution.

As described above, in various embodiments certain functionality may be accessible by a user through a web-based viewer (such as a web browser), or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

In an implementation the irregularity detection system (or one or more aspects of the irregularity detection system) may comprise, or be implemented in, a "virtual computing environment." As used herein, the term "virtual computing environment" should be construed broadly to include, for example, computer readable program instructions executed by one or more processors (e.g., as described herein in the example of FIG. 8) to implement one or more aspects of the modules and/or functionality described herein. Further, in this implementation, one or more modules and/or functionality of the irregularity detection system 132 may be understood as comprising one or more rules engines of the virtual computing environment that, in response to inputs received by the virtual computing environment, execute rules and/or other program instructions to modify operation of the virtual computing environment. For example, performing data ingestion, including decoding, dereferencing and normalization, calculating aggregate values and/or statistical quantities on ingested data, and presenting data items and/or aggregate values and statistical quantities to a user in a graphical user interface, etc., may be understood as modifying operation of the virtual computing environment to create different outputs. Such functionality may comprise a modification of the operation of the virtual computing environment in response to inputs and according to various rules. Other functionality implemented by the virtual computing environment (as described throughout this disclosure) may further comprise modifications of the operation of the virtual computing environment, for example, the operation of the virtual computing environment may change depending on the information gathered or generated by the system. Initial operation of the virtual computing environment may be understood as an establishment of the virtual computing environment. In some implementations the virtual computing environment may comprise one or more virtual machines or other emulations of a computing system. In some implementations the virtual computing environment may comprise a hosted computing environment that includes a collection of physical computing resources that may be remotely accessible and may be rapidly provisioned as needed (commonly referred to as "cloud" computing environment).

Implementing one or more aspects of the irregularity detection system 132 as a virtual computing environment may advantageously enable executing different aspects or modules of the system on different computing devices or processors, which may increase the scalability of the system. Implementing one or more aspects of the irregularity detection system 132 as a virtual computing environment may further advantageously enable sandboxing various aspects, data, or modules of the system from one another, which may increase security of the system by preventing, e.g., malicious intrusion into the system from spreading. Implementing one or more aspects of the irregularity detection system 132 as a virtual computing environment may further advantageously enable parallel execution of various aspects or modules of the system, which may increase the scalability of the system. Implementing one or more aspects of the irregularity detection system 132 as a virtual computing environment may further advantageously enable rapid provisioning (or de-provisioning) of computing resources to the system, which may increase scalability of the system by, e.g., expanding computing resources available to the system or duplicating operation of the system on multiple computing resources. For example, the system may be used by thousands, hundreds of thousands, or even millions of users simultaneously, and many megabytes, gigabytes, or terabytes (or more) of data may be transferred or processed by the system, and scalability of the system may enable such operation in an efficient and/or uninterrupted manner.

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method comprising:
   receiving a file comprising a plurality of records, the plurality of records comprising: (i) a first record associated with a first person and a first provider, and (ii) a second record associated with a second person and a second provider, the first person different from the second person;
   determining a first format of the plurality of records;
   converting, from the first format into a standard format, (i) the first record to a first data item and (ii) the second record to a second data item, wherein converting the first record to the first data item further comprises:
      applying a regular expression to a data value of the first record;
      receiving a match between the regular expression and the data value; and
      assigning text to a data field in the first data item based at least in part on receiving the match between the regular expression and the data value; and
   causing presentation, in a first user interface, of a statistical measure based at least in part on a plurality of data items comprising at least one of the first data item or the second data item,
   wherein the method is performed by one or more computer hardware processors.

2. The method of claim 1, further comprising:
   causing presentation, in a second user interface, of a table comprising the plurality of data items;
   receiving, via the second user interface, a filter parameter;
   determining, from the plurality of data items, a subset of data items associated with the filter parameter; and
   causing presentation, in the second user interface, of the subset of data items in the table.

3. The method of claim 1, further comprising:
   causing presentation, in a second user interface, of a graph based at least in part on the plurality of data items.

4. The method of claim 1, further comprising:
   receiving, in the first user interface, user input indicating receive a selection of the first provider;
   determining, from the plurality of data items, a subset of data items associated with the first provider, the subset of data items (i) including the first data item and (ii) excluding the second data item; and
   causing presentation, in a second user interface, of a visualization based at least in part on the subset of data items associated with the first provider.

5. The method of claim 4, wherein the visualization comprises at least one of a plot, a graph, or a chart.

6. The method of claim 1, wherein converting the first record to the first data item further comprises:
   identifying, from a description mapping list, a first mapping between the text and the regular expression.

7. The method of claim 1, wherein converting the second record to the second data item further comprises:
   identifying a data type for a second data value of the second record;
   calculating, based at least in part on the data type, a converted value from the second data value; and
   assigning the converted value to a second data field in the second data item.

8. The method of claim 7, wherein calculating the converted value further comprises:
   at least one of, multiplying or dividing the second data value by a conversion factor.

9. A system comprising:
   a computer readable storage medium having program instructions embodied therewith; and
   one or more processors configured to execute the program instructions to cause the system to:
      receive a file comprising a plurality of records, the plurality of records comprising: (i) a first record associated with a first person and a first provider, and (ii) a second record associated with a second person and a second provider, the first person different from the second person;
      determine a first format of the plurality of records;
      convert, from the first format into a standard format, (i) the first record to a first data item and (ii) the second record to a second data item, wherein converting the first record to the first data item further comprises:
         applying a regular expression to a data value of the first record;

receiving a match between the regular expression and the data value; and assigning text to a data field in the first data item based at least in part on receiving the match between the regular expression and the data value; and cause presentation, in a first user interface, of a statistical measure based at least in part on a plurality of data items comprising at least one of the first data item or the second data item.

10. The system of claim 9, wherein the one or more processors are configured to execute additional program instructions to cause the system to:

cause presentation, in a second user interface, of a table comprising the plurality of data items;

receive, via the second user interface, a filter parameter;

determine, from the plurality of data items, a subset of data items associated with the filter parameter; and cause presentation, in the second user interface, of the subset of data items in the table.

11. The system of claim 9, wherein the one or more processors are configured to execute additional program instructions to cause the system to:

cause presentation, in a second user interface, of a graph based at least in part on the plurality of data items.

12. The system of claim 9, wherein the one or more processors are configured to execute additional program instructions to cause the system to:

receive, in the first user interface, user input indicating receive a selection of the first provider;

determine, from the plurality of data items, a subset of data items associated with the first provider, the subset of data items (i) including the first data item and (ii) excluding the second data item; and cause presentation, in a second user interface, of a visualization based at least in part on the subset of data items associated with the first provider.

13. The system of claim 12, wherein the visualization comprises at least one of a plot, a graph, or a chart.

14. The system of claim 9, wherein converting the first record to the first data item further comprises:

identifying, from a description mapping list, a first mapping between the text and the regular expression.

15. The system of claim 9, wherein converting the second record to the second data item further comprises:

identifying a data type for a second data value of the second record;

calculating, based at least in part on the data type, a converted value from the second data value; and assigning the converted value to a second data field in the second data item.

16. The system of claim 15, wherein calculating the converted value further comprises:

at least one of, multiplying or dividing the second data value by a conversion factor.

* * * * *